United States Patent [19]

Aumueller et al.

[11] Patent Number: 5,017,702

[45] Date of Patent: May 21, 1991

[54] 2,6-POLYALKYL-4-PIPERIDYLAMIDES, USE THEREOF AS STABILIZERS, IN PARTICULAR FOR PLASTICS, AND ORGANIC MATERIAL CONTAINING SAME

[75] Inventors: Alexander Aumueller, Diedesheim; Peter Neumann, Mannheim; Hubert Trauth, Dudenhofen, all of Fed. Rep. of Germany

[73] Assignee: BASF Aktiengesellschaft, Ludwigshafen, Fed. Rep. of Germany

[21] Appl. No.: 375,874

[22] Filed: Jul. 6, 1989

[30] Foreign Application Priority Data

Jul. 8, 1988 [DE] Fed. Rep. of Germany ....... 3823112

[51] Int. Cl.⁵ .................. C07D 401/12; C07D 401/14; C07D 221/14; C07D 211/58
[52] U.S. Cl. ......................... 546/99; 546/16; 546/187; 546/190; 546/193; 546/194; 546/212; 546/213; 546/214; 546/224; 546/244
[58] Field of Search ............ 546/99, 16, 187, 190, 546/200, 224, 244, 193, 194, 212, 213, 214

[56] References Cited

U.S. PATENT DOCUMENTS 3,684,765 8/1972 Matsui .......................... 260/45.8 N
3,755,586 8/1973 Sanzari .............................. 514/516

FOREIGN PATENT DOCUMENTS 117225 8/1984 European Pat. Off. .
172413 2/1986 European Pat. Off. .
2040975 2/1972 Fed. Rep. of Germany .

*Primary Examiner*—Mark L. Berch
*Attorney, Agent, or Firm*—Oblon, Spivak, McClelland, Maier & Neustadt

[57] ABSTRACT

Useful stabilizers for organic material, in particular plastics and paints, and metal ion deactivators are amides of the formula

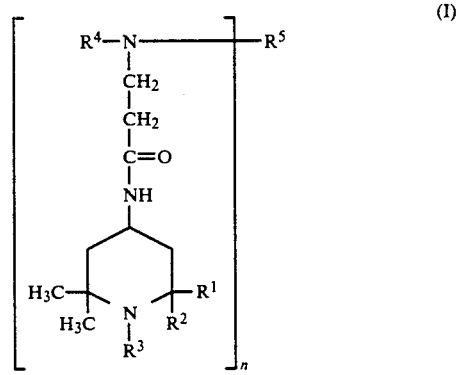

where $R^1$ and $R^2$ are singly methyl or together tetramethylene or pentamethylene, $R^3$ is hydrogen, alkyl, alkoxycarbonyl, alkanoyl, benzyl, hydroxyethyl, cyanomethyl or aminomethyl, n is 1, 2 or 3 and—when n is 1—$R^4$ is hydrogen and $R^5$ is —CO—$R^6$ is H, alkyl, cycloalkyl, aralkyl, phenoxyalkyl, aryl, a 5- or 6-membered heterocycle, alkoxy, aryloxy, cycloalkyloxy, phenylalkoxy, carbamoyl or —SO₂—$R^8$ where $R^8$ is alkyl or phenyl or

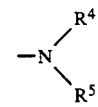

is a phthalimide group or—when n is 2—$R^4$ is H and $R^5$ is —CO—Z—CO— where Z is a chemical bond, C₁-C₈-alkylene, oxaalkylene, phenylene, cyclohexylene, biphenylene, biphenylene oxide, dioxyphenylene, diaminophenylene, diaminocyclohexylene, 1-Ω-diiminoalkylene or a 2-valent heterocycle or

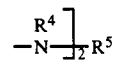

is a pyromellimide group or—when n is 3—$R^4$ is H and $R^5$ is

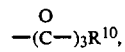

where $R^{10}$ is a trivalent alkyl or 3-valent aryl, or acid addition salts and hydrates thereof.

4 Claims, No Drawings

2,6-POLYALKYL-4-PIPERIDYLAMIDES, USE THEREOF AS STABILIZERS, IN PARTICULAR FOR PLASTICS, AND ORGANIC MATERIAL CONTAINING SAME

It is known that polyalkylpiperidine derivatives protect organic polymers from destruction by light and heat.

Such stabilizers are known for example from DE-A-2,349,962.

Unsatisfactory aspects of prior art stabilizers are frequently their poor compatibility with polyolefins and other plastics, the duration of the protection, and their volatility and decomposition on incorporation at elevated temperatures, in particular in aggressive polymer media.

It is an object of the present invention to provide novel stabilizers which are free of the above-mentioned disadvantages.

We have found that this object is achieved with the novel polyalkylpiperidylamides. The present invention accordingly provides novel compounds of the general formula (I)

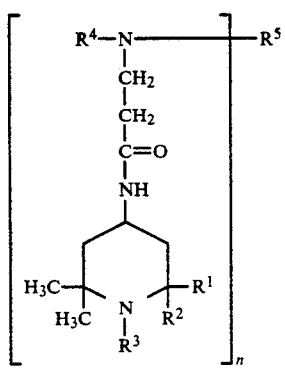

where $R^1$ and $R^2$ are singly methyl or together tetramethylene or pentamethylene, $R^3$ is hydrogen, $C_1$-$C_8$-alkyl, $C_1$-$C_8$-alkoxycarbonyl, $C_1$-$C_8$-alkanoyl, benzyl, hydroxyethyl, cyanomethyl or aminoethyl, n is 1, 2 or 3, and— when n is 1—

$R^4$ is hydrogen and $R^5$ is (a) 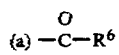

where $R^6$ is hydrogen, $C_1$-$C_{19}$-alkyl, $C_7$-$C_{10}$-phenylalkyl where the phenyl nucleus may be monosubstituted, disubstituted or trisubstituted by $C_1$-$C_8$-alkyl, chlorine, bromine, fluorine, hydroxyl, $C_1$-$C_4$-alkoxy, phenyl, phenoxy or carboxyl and the substituents can be identical or different, phenoxy-$C_1$-$C_4$-alkyl, unsubstituted or $C_1$-$C_8$-alkyl-monosubstituted, -disubstituted or -trisubstituted $C_3$-$C_{10}$-cycloalkyl, unsubstituted or $C_1$-$C_8$-alkyl-, chlorine-, bromine-, fluorine-, hydroxyl-, $C_1$-$C_4$-alkoxy-, phenyl-, phenoxy- or carboxyl-monosubstituted, -disubstituted or -trisubstituted phenol naphthyl, a 5- or 6-membered saturated or aromatic O-, S- or N-containing heterocycle which may be monosubstituted, disubstituted, trisubstituted or tetrasubstituted by $C_1$-$C_4$-alkyl, or $C_1$-$C_{18}$-alkoxy where the alkyl chain may be interrupted by —O—, or phenoxy, naphthoxy, unsubstituted or $C_1$-$C_4$-alkylmonosubstituted or -disubstituted $C_5$- or $C_6$-cycloalkoxy or phenylalkoxy of from 7 to 12 carbon atoms in total, (b) —CO—NH—$R^7$ where $R^7$ is hydrogen, $C_1$-$C_{18}$-alkyl, $C_5$- or $C_6$-cycloalkyl, phenyl which may be monosubstituted, disubstituted or trisubstituted by $C_1$-$C_8$-alkyl, chlorine, bromine, fluorine or $C_1$-$C_4$-alkoxy, or phenyl-$C_1$-$C_4$-alkyl, or (c) —$SO_2$—$R^8$ where $R^8$ is $C_1$-$C_{18}$-alkyl or unsubstituted or $C_1$-$C_4$-alkyl- or chlorine-substituted phenyl, or

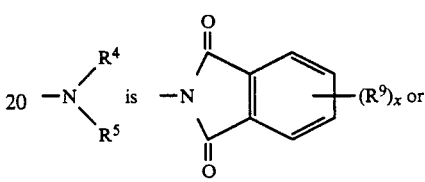

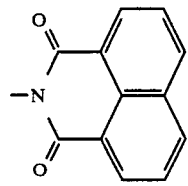

$C_1$-$C_8$-alkyl, chlorine, bromine or fluorine and x is 0, 1, 2, 3 or 4, or—when n is 2—

$R^4$ is hydrogen and $R^5$ is

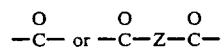

where

Z is a chemical bond, $C_1$-$C_{12}$-alkylene, $C_4$-$C_8$-oxaalkylene, phenylene, cyclohexylene, biphenylene, biphenylene oxide, dioxyphenylene, diaminophenylene, diaminocyclohexylene,

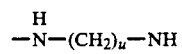

where u is from 2 to 6, —O—X—O—, where X is $C_2$-$C_8$-alkylene or $C_4$-$C_8$-oxaalkylene or a bivalent saturated or unsaturated 5- or 6-membered O-, S- or N-containing heterocycle, or

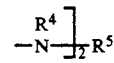

is a pyromellimide group,
or—when n is 3—
$R^4$ is hydrogen and
$R^5$ is

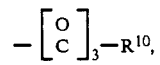

where $R^{10}$ is trivalent $C_1$–$C_8$-alkyl or trivalent aryl, and acid addition salts and hydrates of compounds (I).

Compounds (I) according to the invention stabilize organic material, specifically plastics, against degradation by light and heat. They also act as metal deactivators. They are added to the plastics to be stabilized in a concentration of from 0.01 to 5% by weight, preferably from 0.02 to 2% by weight, before, during or after polymer formation.

In the polymer the polyalkylpiperidylamides (I) have good stabilizing properties combined with excellent compatibility. Particularly good properties are possessed by compounds (I) according to the invention in polyolefins, in particular in ethylene and propylene polymers, and in polyamides, but also in polyurethanes and paints.

$R^1$ and $R^2$ are each preferably methyl.

Alkyl $R^3$ can be linear or branched. Specific examples of alkyl are: methyl, ethyl, isopropyl, propyl, butyl, isobutyl, pentyl, hexyl, heptyl and octyl, of which methyl is preferred. Alkyloxycarbonyl $R^3$ is for example methoxycarbonyl, ethoxycarbonyl, propoxycarbonyl, butoxycarbonyl, pentoxycarbonyl, hexoxycarbonyl, heptoxycarbonyl and octoxycarbonyl, of which methoxycarbonyl is preferred.

Arcy $R^3$ is $C_1$–$C_8$-alkznoyl, for example propinoyl, butanoyl, pentanoyl, hexanoyl, heptanoyl or octanoyl, preferably acetyl.

$R^3$ can also be benzyl, hydroxyethyl, aminoethyl or cyanomethyl.

Particularly preferred $R^3$ is hydrogen.

When n is 1, $R^5$ is for example:

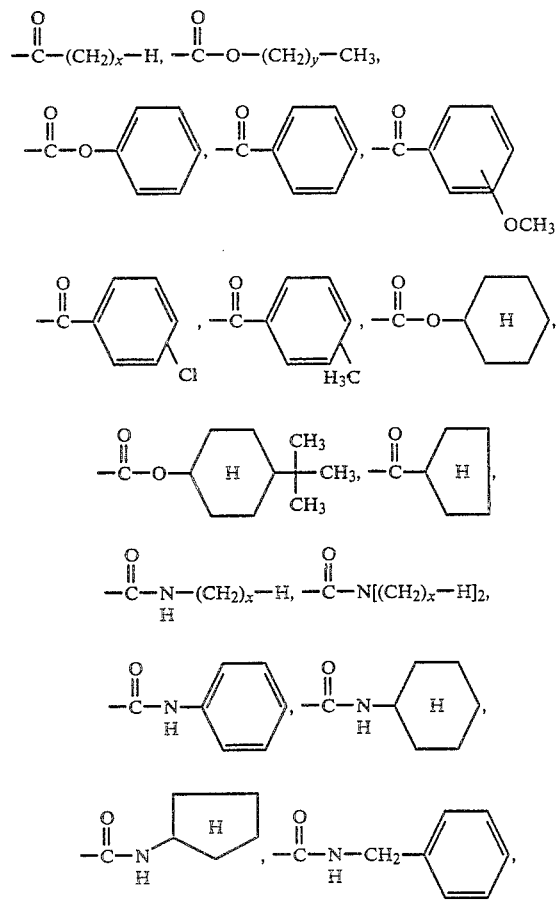

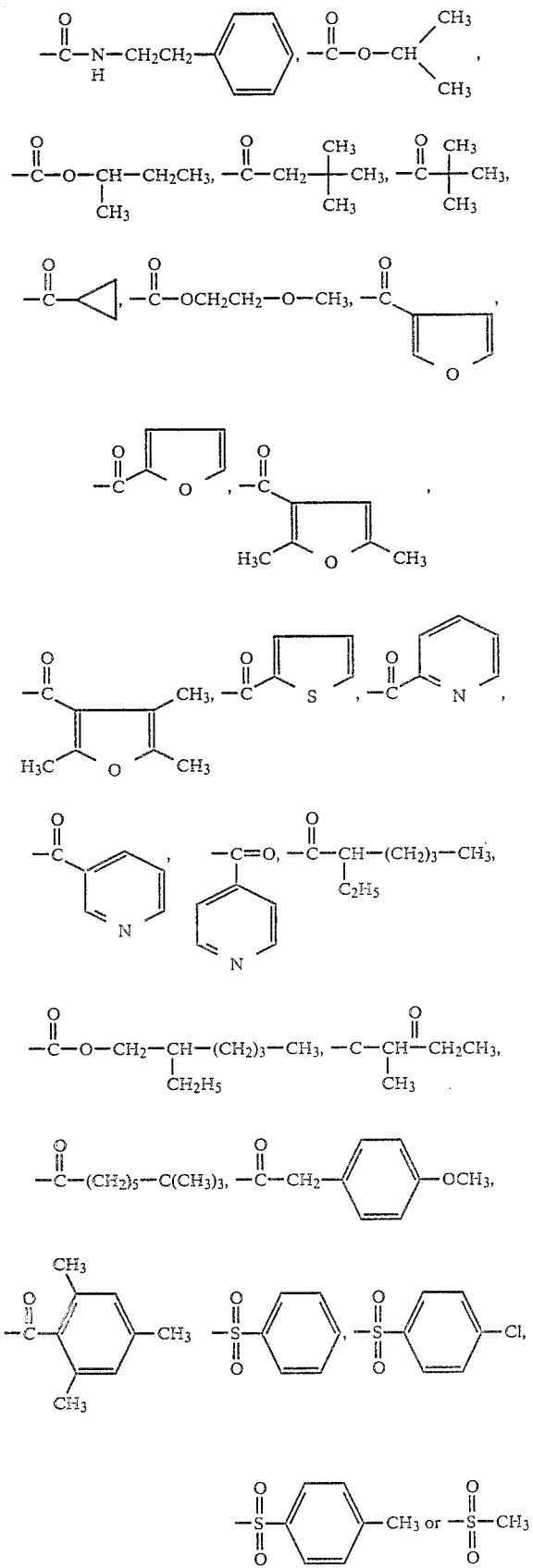

where x is from 0 to 20 and y is from 0 to 16. When n is 1,

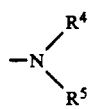

can for example also be a group of the formula:

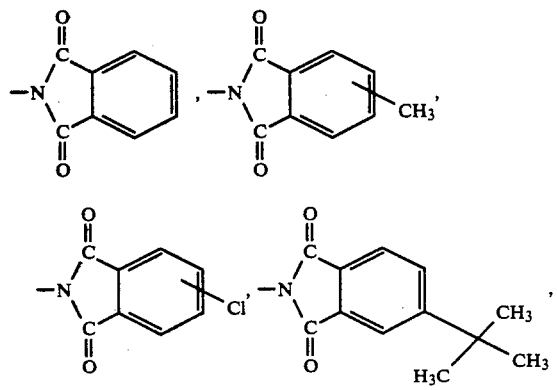

When n is 2 and $R^4$ is hydrogen, the $R^5$ can be for example:

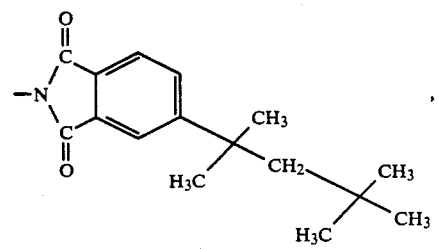

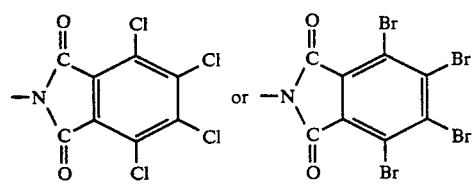

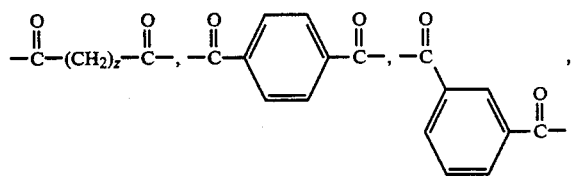

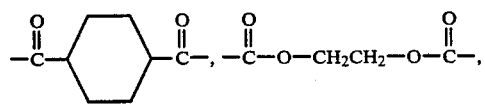

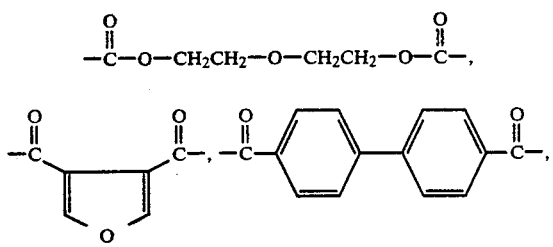

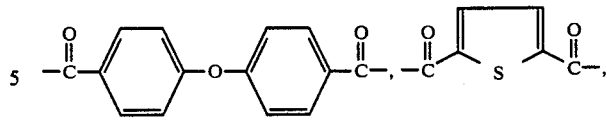

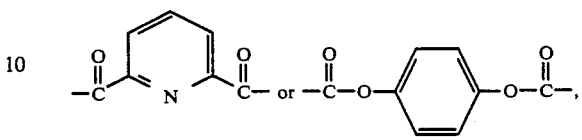

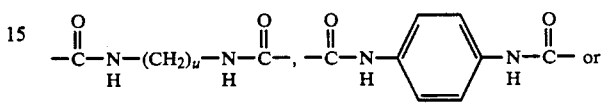

where z is from 1 to 12 and u is from 2 to 6.

$R^4$ and $R^5$ can also be together for example a group of the formula

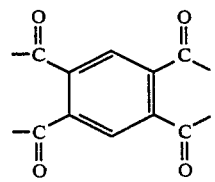

When n is 3 and $R^4$ is hydrogen, then $R^5$ can be for example

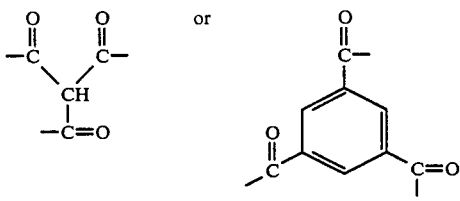

The compounds according to the invention are preparable in a conventional manner for example by reacting compounds of the general formula (II)

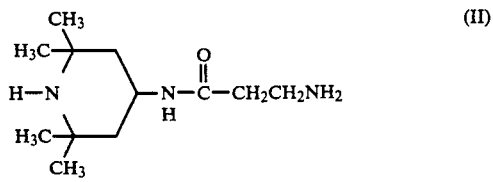

(II)

with such carboxylic acids, carboxylic anhydrides, carboxylic esters, sulfonyl chlorides, chloroformates, ureas or isocyanates as correspond to $R^5$.

In this reaction, it is possible to use for example an auxiliary base, for example a tertiary amine such as triethylamine or pyridine.

Preference is given to working in inert organic solvents, for example dichloromethane, chloroform, carbon tetrachloride, benzene, toluene, xylene, acetonitrile, tetrahydrofuran or diethyl ether or else ethyl acetate or butyl acetate.

The reaction can be carried out within the temperature range from −20° C. to 100° C., preferably at from 0° C. to 25° C.

Compounds of the general formula (I) where $R^3$ is H are convertible into compounds of the general formula (I) where $R^3$ is not H by methods described in the literature, for example by acylation, alkylation, cyanomethylation or ethoxylation.

The compounds according to the invention can be present in the form of the free bases, as hydrates or as salts. Suitable anions come for example from inorganic acids and in particular from organic carbon, or carboxylic, acids and also from organic sulfonic acids.

Inorganic anions are for example chloride, bromide, sulfate, methosulfate, tetrafluoroborate, phosphate and thiocyanate.

Carboxylic acid anions are for example formate, acetate, propionate, hexanoate, cyclohexanoate, lactate, stearate, dodecylbenzoate, benzoate, acrylate, methacrylate, citrate, malonate and succinate and also anions of polycarboxylic acids having up to 3000 COOH groups.

Sulfonic acid anions are for example benzenesulfonate and tosylate.

The plastics stabilized by the compounds (I) may additionally contain further additives, for example antioxidants, light stabilizers, metal deactivators, antistats, flame retardants and also pigments and fillers.

The novel compounds (I) can be incorporated into the plastics to be stabilized with or without other stabilizing agents and/or additives in a conventional manner and in conventional equipment.

Antioxidants and light stabilizers which may be added to the plastics as well as the compounds according to the invention are for example compounds based on sterically hindered phenols or sulfur- or phosphorus-containing costabilizers.

Such phenolic antioxidants are for example: 2,6-di-tert-butyl-4-methylphenol, n-octadecylβ-(3,5-di-tertbutyl-4-hydroxyphenyl)propionate, 1,1,3-tris(2-methyl-4-hydroxy-5-tert-butylphenyl)butane, 1,3,5-trimethyl-2,4,6tris(3′,5′-di-tert-butyl-4′-hydroxybenzyl)benzene, 1,3,5tris(3′,5′-di-tert-butyl-4-hydroxybenzyl) isocyanurate, 1,3,5-tris[β-(3′,5′-di-tert-butyl-4′-hydroxyphenyl)-propionyloxyethyl]isocyanurate, 1,3,5-tris-(2′,6′-dimethyl-3′-hydroxy-4′-tert-butylbenzyl) isocyanurate and pentaerythritol tetrakis[β-(3,5-di-tert-butyl-4-hydroxyphenyl)propionate].

Phosphorus-containing antioxidants are for example tris(nonylphenyl) phosphite, distearyl pentaerythritol diphosphite, tris(2,4-ditert-butylphenyl) phosphite, tris(2-tert-butyl-4-methylphenyl) phosphite, bis-(2,4-di-tert-butylphenyl)pentaerythritol diphosphite and tetrakis(2,4-di-tert-butylphenyl) 4,4′-biphenylene diphosphite.

Sulfur-containing antioxidants are for example: dilauryl thiodipropionate, dimyristyl thiodipropionate, distearyl thiodipropionate, pentaerythritol tetrakis-(β-laurylthiopropionate) and pentaerythritol tetrakis-(β-hexylthiopropionate).

Further antioxidants and light stabilizers which may be used together with the compounds (I) according to the invention are for example 2-(2′-hydroxyphenyl)benzotriazoles, 2-hydroxybenzophenones, aryl esters of hydroxybenzoic acids, α-cyanocinnamic acid derivatives, nickel compounds, oxalic dianilides and benzimidazolecarboxanilides.

Organic polymers which can be stabilized with the compounds according to the invention are for example:

polymers of mono- and diolefins, for example polyethylene of low or high density, linear polyethylene of low density, polypropylene, polyisobutylene, polybutene-1, polyisoprene, polybutadiene and copolymers of mono- or diolefins or mixtures thereof;

copolymers of mono- or diolefins with other vinyl monomers such as ethylene/alkyl acrylate copolymers, ethylene/alkyl methacrylate copolymers, ethylene/vinyl acetate copolymers or ethylene/acrylic acid copolymers;

polystyrene;

copolymers of styrene or α-methylstyrene with dienes or acrylic derivatives, for example styrenebutadiene, styrene-acrylonitrile, styrene-/ethyl methacrylate, styrene/butadiene/ethyl acrylate, styrene/acrylonitrile/methacrylate;

ABS, MBS or similar polymers;

halogen-containing polymers, for example polyvinyl chloride, polyvinyl fluoride, polyvinylidene fluoride and copolymers thereof;

polymers derived from α,β-unsaturated acids and derivatives thereof, such as polyacrylates and polymethacrylates, polyacrylamides and polyacrylonitriles;

polymers derived from unsaturated alcohols and amines or acrylic derivatives or acetals thereof, such as polyvinyl alcohol or polyvinyl acetate;

polyurethanes, polyamides, polyureas, polyesters, polycarbonates, polysulfones, polyether sulfones and polyether ketones.

It is also possible to stabilize paint films against degradation by light and heat with compounds (I). Particularly notable paint films are baking finishes, in particular automotive coatings, preferably two-layer coatings. Here too, it is possible to use in addition the abovementioned antioxidants and light stabilizers.

The compounds according to the invention can be added to paints in solid or dissolved form. In this their ready solubility in paint systems is of particular advantage.

The Examples further illustrate the invention. In no case have the yields of the Preparation Examples been optimized.

PREPARATION EXAMPLES

EXAMPLE 1

800 ml of ethanol, 1356 g of ethyl cyanoacetate and 1860 g of 2,2,6,6-tetramethyl-4-aminopiperidine were boiled for 7 hours and then cooled down in an ice bath to 10° C. The resulting precipitate was filtered off with suction and washed with cold ethyl acetate, leaving 1588 g of the compound of the formula

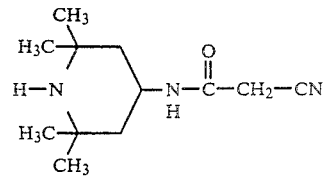

as a colorless solid of melting point 148° C.

EXAMPLE 2

150 g of the product of Example 1 were hydrogenated at 100° C. under a hydrogen pressure of 300 bar to constant pressure in the presence of 25 g of Raney nickel and 100 g of ammonia in 1000 ml of toluene. The reaction mixture was filtered, and the filtrate was concentrated to leave 150 g of the compound of the formula

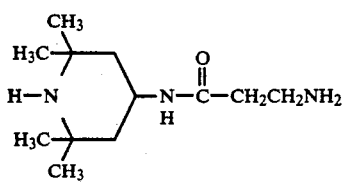

which solidifies on prolonged standing and has a melting point of 59°-60° C.

EXAMPLE 3

34.0 g of the product of Example 2 and 15.2 g of triethylamine were dissolved in 150 ml of dichloromethane. 11.8 g of acetyl chloride in 100 ml of dichloromethane were added dropwise at 0° C., and the mixture was warmed to room temperature. The reaction mixture was subsequently stirred for 5 hours and then evaporated, the residue was dissolved in water, and the solution was made alkaline with sodium hydroxide solution. The aqueous phase was extracted with n-butanol, and the n-butanol phase was washed with water and concentrated. The residue was recrystallized from acetonitrile, giving 26 g of the compound of the formula

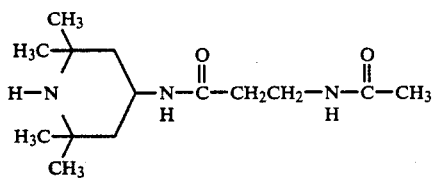

as a colorless solid of melting point 152° C.
Calculated: C 62.4 H 10.1 N 15.6 O 11.9%
Found: C 62.1 H 9.9 N 15.6 O 12.0%

EXAMPLE 4

13.9 g of propionyl chloride in 100 ml of dichloromethane were added dropwise at 0° C. to 34 g of the product of Example 2 and 16.0 g of triethylamine in 200 ml of dichloromethane. After 3 hours at room temperature, 20 g of NaOH, dissolved in 300 ml of water, were added. The organic phase was separated off, dried over magnesium sulfate and concentrated. The residue was recrystallized from toluene, giving 9.1 g of the compound of the formula

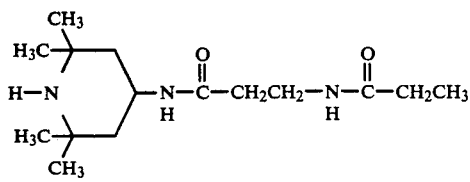

as a colorless solid of melting point 149°-153° C.
Calculated: C 63.6 H 10.3 N 14.8 O 11.3%
Found: C 62.7 H 10.3 N 14.5 O 12.3%

EXAMPLE 5

34.0 g of the product of Example 2, 16.0 g of triethylamine and 16.0 g of butyryl chloride were reacted and worked up, both steps being carried out as described in Example 4. Recrystallization from acetonitrile gave 23.1 g of the compound of the formula

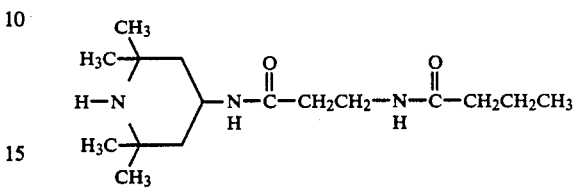

as a colorless solid of melting point 180-81° C.
Calculated: C 64.6 H 10.5 N 14.1 O 10.8%
Found: C 64.5 H 10.4 N 14.1 O 10.7%

EXAMPLE 6

18.1 g of pivaloyl chloride in 100 ml of dichloromethane were added dropwise at 0° C. to 34.0 g of the product of Example 2 and 16.0 g of triethylamine in 200 ml of dichloromethane. After 3 hours' stirring at room temperature, 20 g of sodium hydroxide, dissolved in 500 ml of water, were added and the phases were separated. The aqueous phase was extracted with n-butanol, and the organic phases were combined, dried over magnesium sulfate, filtered and concentrated. The residue was recrystallized from acetonitrile, giving 25.9 g of the compound of the formula

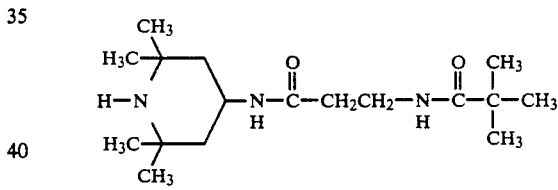

as a colorless solid of melting point 177°-178° C.
Calculated: C 65.6 H 10.7 N 13.5 O 10.3%
Found: C 65.5 H 10.7 N 13.4 O 10.1%

EXAMPLE 7

34.0 g of the product of Example 2, 16.0 g of triethylamine and 20.2 g of tert-butylacetyl chloride were reacted and worked up, both steps being carried out as described in Example 4. Recrystallization from acetonitrile gave 24.1 g of the compound of the formula

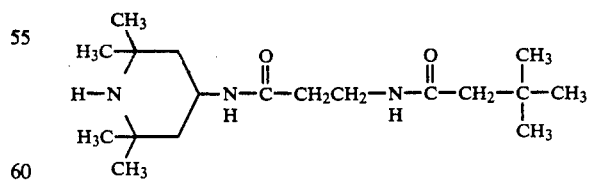

as a colorless solid of melting point 148°-151° C.
Calculated: C 66.4 H 10.8 N 12.9 O 9.8%
Found: C 66.2 H 10.8 N 13.0 O 9.7%

EXAMPLE 8

24.4 g of 2-ethyl-1-hexanoyl chloride in 100 ml of dichloromethane were added dropwise at 0° C. to 34.0 g of the product of Example 2 and 15.2 g of triethylamine in 400 ml of dichloromethane. After 4 hours at room temperature, the reaction mixture was evaporated to dryness, the residue was suspended in water, and the suspension was made alkaline with sodium hydroxide solution. The solids were filtered off with suction and washed with water, and the residue was recrystallized from acetonitrile, giving 39 g of the compound of the formula

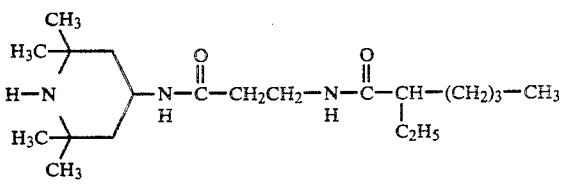

as a colorless solid of melting point 192° C.
Calculated: C 67.9 H 11.1 N 11.9 O 9.0%
Found: C 67.9 H 11.1 N 11.9 O 8.9%

EXAMPLE 9

26.0 g of benzoyl chloride in 100 ml of dichloromethane were added dropwise at 0° C. to 42.0 g of the product of Example 2 and 18.7 g of triethylamine in 150 ml of dichloromethane. After 2 days at room temperature, 200 ml of petroleum ether were added, and the resulting precipitate was filtered off with suction and dissolved in water. The solution was rendered alkaline with sodium hydroxide solution and extracted with n-butanol. After the n-butanol had been evaporated off, the residue was recrystallized from acetonitrile. This gave 50.0 g of the compound of the formula

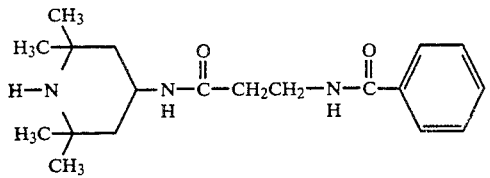

as a colorless solid of melting point 190° C.
Calculated: C 68.8 H 8.8 N 12.7 O 9.6%
Found: C 68.5 H 8.9 N 12.8 O 9.7%

EXAMPLE 10

27.4 g of 2,4,6-trimethylbenzoyl chloride in 75 ml of dichloromethane were added dropwise at 0° C. to 34.5 g of the product of Example 2 and 15.2 g of triethylamine in 200 ml of dichloromethane. After 16 hours' stirring at room temperature, the precipitate was filtered off with suction, washed with dichloromethane and suspended in 250 ml of water. The suspension was made alkaline with sodium hydroxide solution, and the suspended solids were filtered off with suction and washed with a little water. Recrystallization from acetonitrile gave 12.0 g of the compound of the formula

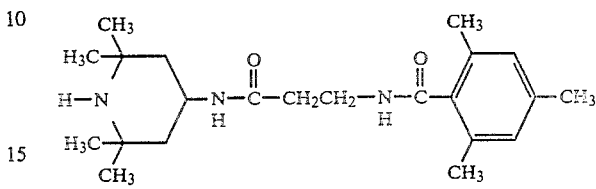

as a colorless solid of melting point 229° C.
Calculated: C 70.7 H 9.4 N 11.2 O 8.6%
Found: C 70.7 H 9.5 N 11.2 O 8.6%

EXAMPLE 11

45.8 g of the product of Example 2 and 5.9 g of urea were mixed and heated at 130°–140° C. for 7 hours. Cooling down was followed by recrystallization from acetonitrile. This gave 24.0 g of the compound of the formula

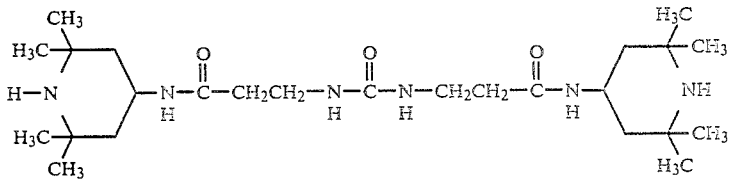

as a colorless solid of melting point 217° C.
Calculated: C 62.5 H 10.1 N 17.5 O 10.0%
Found: C 62.0 H 10.1 N 17.5 O 10.3%

EXAMPLE 12

8.4 g of oxalyl dichloride in 50 ml of dichloromethane were added dropwise at 0° C. to 33 g of the product of Example 2 and 13.6 g of triethylamine in 200 ml of dichloromethane. After 2 days at room temperature, the solids were filtered off with suction, washed with dichloromethane, dissolved in 250 ml of water, rendered alkaline with sodium hydroxide solution and extracted with n-butanol. The butanol phase was concentrated, the oily residue was dissolved in 250 ml of hot methyl tertbutyl ether, and the solution was added dropwise to 1.21 of petroleum ether. The precipitated residue was filtered off with suction and dissolved in 250 ml of acetonitrile. Insolubles were filtered off at 5° C., the acetonitrile filtrate was concentrated, and the residue was recrystallized from ethyl acetate. This gave 6.1 g of the compound of the formula

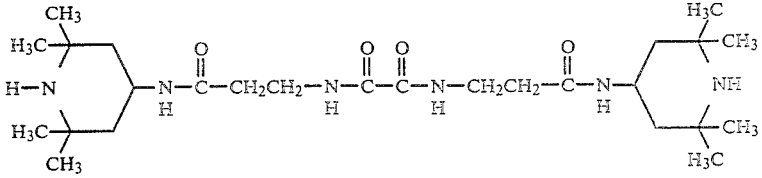

as a colorless solid of melting point 203° C.

Calculated: C 61.4 H 9.5 N 16.5 O 12.6%
Found: C 61.4 H 9.7 N 16.6 O 12.7%

EXAMPLE 13

11.3 g of adipoyl dichloride in 40 ml of dichloromethane were added dropwise at 0° C. to 31.0 g of the product of Example 2 and 13.7 g of triethylamine in 100 ml of dichloromethane. After 3 days of stirring at room temperature, the resulting precipitate was filtered off with suction, washed with dichloromethane and dissolved in water. The solution was rendered alkaline with sodium hydroxide solution and extracted with n-butanol, and the organic phase was evaporated. Recrystallization from isopropanol in the presence of activated carbon gave 11.0 g of the compound of the formula

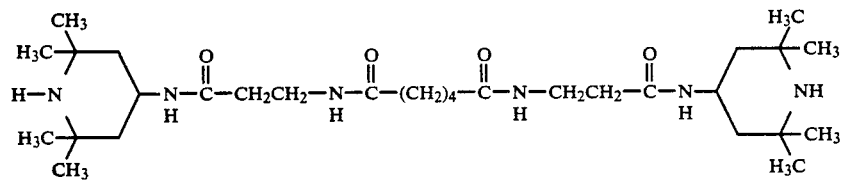

as a colorless solid of melting point 243° C. (dec.)
Calculated: C 63.8 H 10.0 N 14.9 O 11.3%
Found: C 63.4 H 9.9 N 14.7 O 11.4%

EXAMPLE 14

9.9 g of 1,5-pentanedicarbonyl dichloride in 50 ml of dichloromethane were added dropwise to 22.7 g of the product of Example 2 and 11.0 g of triethylamine in 200 ml of dichloromethane. After 3 hours of stirring at room temperature, 500 ml of water were added. The phases were separated, and the aqueous phase was rendered alkaline with sodium hydroxide solution and extracted with n-butanol, and the n-butanol was distilled off. Recrystallization of the residue from toluene gave 3.5 g of the compound of the formula

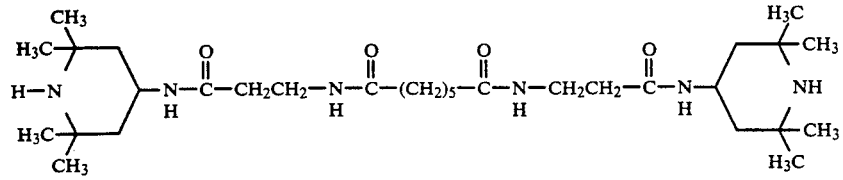

as a colorless solid of melting point 163°-165° C.

Calculated: C 64.3 H 10.1 N 14.5 O 11.1%
Found: C 63.6 H 10.0 N 14.2 O 12.1%
The compound contained water of crystallization.

EXAMPLE 15

22.7 g of the product of Example 2 and 11.0 g of triethylamine were reacted with 10.6 g of suberoyl dichloride and worked up, both steps being carried out as described in Example 15. Recrystallization from toluene gave 12.6 g of the compound of the formula

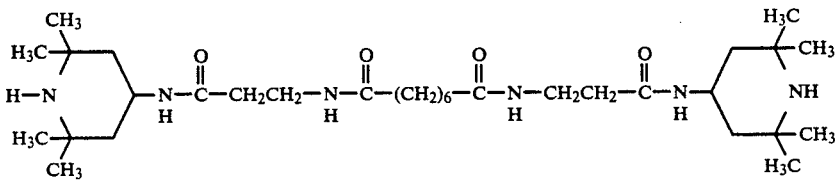

as a colorless solid of melting point 165°-169 C.
Calculated: C 64.8 H 10.2 N 14.2 O 10.8%
Found: C 63.7 H 10.2 N 13.7 O 12.1%
The compound contained water of crystallization.

EXAMPLE 16

17.0 g of sebacoyl dichloride in 50 ml of dichloromethane and 15.1 g of triethylamine in 40 ml of dichloromethane were added dropwise at 0° C. to 34 g of the product of Example 2 in 125 ml of dichloromethane. After 2 days of stirring at room temperature, the solids were filtered off with suction, and the residue was dissolved in 250 ml of water. After the aqueous phase had been rendered alkaline with sodium hydroxide solution, it was extracted with n-butanol. Evaporation of the n-butanol left as a residue 39 g of the compound of the formula

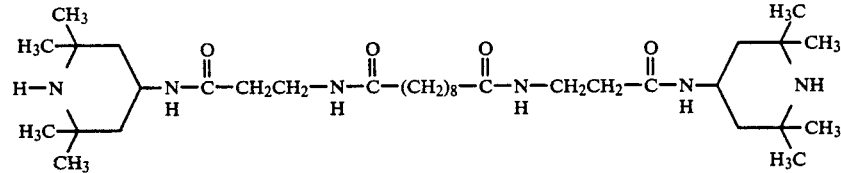

as a colorless solid of melting point 144° C.
Calculated: C 65.8 H 10.4 N 13.5 O 10.3%
Found: C 65.1 H 10.5 N 13.0 O 11.2%
The compound contained water of crystallization.

EXAMPLE 17

32.7 g of the product of Example 2 and 13.5 g of triethylamine were reacted with 13.2 g of terephthaloyl dichloride and worked up, both steps being carried out as described in Example 16. Recrystallization from 1:1 isopropanol/n-butanol gave 19 g of the compound of the formula $$\text{H—N}\underset{\underset{\text{CH}_3}{\overset{\text{H}_3\text{C}}{\Big\rangle}}}{\overset{\overset{\text{CH}_3}{\text{H}_3\text{C}}}{\Big\langle}}\text{—N}\underset{\text{H}}{\text{—}}\overset{\overset{\text{O}}{\|}}{\text{C}}\text{—CH}_2\text{CH}_2\text{—N}\underset{\text{H}}{\text{—}}\overset{\overset{\text{O}}{\|}}{\text{C}}\text{—}\langle\text{phenyl}\rangle\text{—}\overset{\overset{\text{O}}{\|}}{\text{C}}\text{—N}\underset{\text{H}}{\text{—}}\text{CH}_2\text{CH}_2\text{—}\overset{\overset{\text{O}}{\|}}{\text{C}}\text{—N}\underset{\text{H}}{\text{—}}\underset{\underset{\text{H}_3\text{C}}{\overset{\text{H}_3\text{C}}{\Big\rangle}}}{\overset{\overset{\text{CH}_3}{\text{H}_3\text{C}}}{\Big\langle}}\text{NH}$$

as a colorless solid of melting point 262°-263° C.
Calculated: C 65.7 H 9.0 N 14.4 O 10.9%
Found: C 65.2 H 9.1 N 14.2 O 11.3%

EXAMPLE 18

18.1 g of n-propyl chloroformate in 50 ml of dichloromethane were added dropwise at 0° C. to 41 g of the product of Example 2 and 15 g of triethylamine in 250 ml of dichloromethane. After 16 hours of stirring at room temperature, the solvent was evaporated off, and the residue was dissolved in water. The aqueous phase was rendered alkaline with sodium hydroxide solution and extracted with n-butanol. After the n-butanol had been distilled off, the residue was recrystallized twice from methyl tert-butyl ether and then from acetone. This gave 18.0 g of the compound of the formula $$\text{H—N}\langle\text{ring}\rangle\text{—N}\underset{\text{H}}{\text{—}}\overset{\overset{\text{O}}{\|}}{\text{C}}\text{—CH}_2\text{CH}_2\text{—N}\underset{\text{H}}{\text{—}}\overset{\overset{\text{O}}{\|}}{\text{C}}\text{—O—CH}_2\text{CH}_2\text{CH}_3$$

as a colorless solid of melting point 116° C.
Calculated: C 61.3 H 10.0 N 13.4 O 15.3%
Found C 61.3 H 10.0 N 13.5 O 15.1%

EXAMPLE 19

41 g of the product of Example 2 and 17.8 g of triethylamine were reacted with n-butyl chloroformate and worked up, both steps being carried out as described in Example 18. Recrystallization from acetonitrile and washing with petroleum ether gave 22 g of the compound of the formula $$\text{H—N}\langle\text{ring}\rangle\text{—N}\underset{\text{H}}{\text{—}}\overset{\overset{\text{O}}{\|}}{\text{C}}\text{—CH}_2\text{CH}_2\text{—N}\underset{\text{H}}{\text{—}}\overset{\overset{\text{O}}{\|}}{\text{C}}\text{—O—(CH}_2)_3\text{—CH}_3$$

as a colorless solid of melting point 76° C.
Calculated: C 62.3 H 10.1 N 12.8 O 14.6%
Found: C 62.2 H 10.2 N 12.9 O 15.2%

EXAMPLE 20

41.5 g of myristyl chloroformate in 100 ml of dichloromethane were added dropwise at 0° C. to 34 g of the product of Example 2 and 15.2 g of triethylamine in 200 ml of dichloromethane. After 16 hours of stirring at room temperature, 100 ml of water were added, the mixture was rendered alkaline with sodium hydroxide solution, and the phases were separated. The aqueous phase was extracted with n-butanol, and the organic phases were combined and evaporated. The residue was recrystallized from n-heptane to give 56 g of the compound of the formula $$\text{H—N}\langle\text{ring}\rangle\text{—N}\underset{\text{H}}{\text{—}}\overset{\overset{\text{O}}{\|}}{\text{C}}\text{—CH}_2\text{CH}_2\text{—N}\underset{\text{H}}{\text{—}}\overset{\overset{\text{O}}{\|}}{\text{C}}\text{—O—(CH}_2)_{13}\text{—CH}_3$$

as a colorless solid of melting point 58° C.
Calculated: C 69.3 H 11.4 N 8.9 O 10.3%
Found: C 68.9 H 11.4 N 8.8 O 10.4%

EXAMPLE 21

34 g of the product of Examle 2 and 15.2 g of triethylamine were reacted with 45.7 g of cetyl chloroformate and worked up, both steps being carried out as described in Example 20. Recrystallization from n-heptane gave 61 g of the compound of the formula $$\text{H—N}\langle\text{ring}\rangle\text{—N}\underset{\text{H}}{\text{—}}\overset{\overset{\text{O}}{\|}}{\text{C}}\text{—CH}_2\text{CH}_2\text{—N}\underset{\text{H}}{\text{—}}\overset{\overset{\text{O}}{\|}}{\text{C}}\text{—O—(CH}_2)_{15}\text{—CH}_3$$

as a colorless solid of melting point 64° C.
Calculated: C 70.2 H 11.6 N 8.5 O 9.7%

Found: C 70.0 H 11.5 N 8.4 O 9.0%

EXAMPLE 22

34 g of the product of Example 2 and 15.2 g of triethylamine were reacted with 28.9 g of 2-ethylhexyl chloroformate and worked up, both steps being carried out as in Example 20. The oil obtained on evaporation of the solvent was not distillable. It was dissolved in dichloromethane and stirred with activated carbon for 16 hours. Evaporation of the solvent left 42 g of the compound of the formula

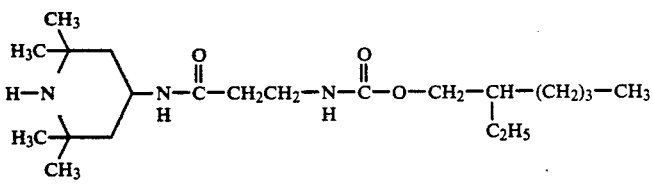

as a viscous, slightly yellowish oil.
Calculated: C 65.8 H 10.8 N 10.9 O 12.5%
Found: C 65.4 H 10.7 N 11.2 O 12.7%

EXAMPLE 23

34.5 g of the product of Example 2 and 15.1 g of triethylamine were reacted with 20.8 g of methoxyethyl chloroformate and worked up, both steps being carried out as in Example 22. This gave 31 g of the compound of the formula

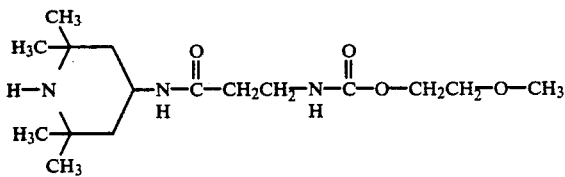

as a highly viscous, slightly yellowish oil which was not distillable.
Calculated: C 58.3 H 9.5 N 12.7 O 19.4%
Found: C 58.3 H 9.5 N 12.7 O 19.5%

EXAMPLE 24

The acid chloride prepared from 19.5 g of heptanoic acid and 23.6 g of thionyl chloride was added dropwise in 100 ml of dichloromethane to 34.0 g of the product of Example 2 and 15 g of triethylamine in 200 ml of dichloromethane. After 4 hours of stirring at room temperature, ice-water was added, the mixture was rendered alkaline with sodium hydroxide solution, and the organic phase was separated off and dried over magnesium sulfate. The solvent was evaporated, and the residue was recrystallized from acetonitrile to give 30.4 g of the compound of the formula

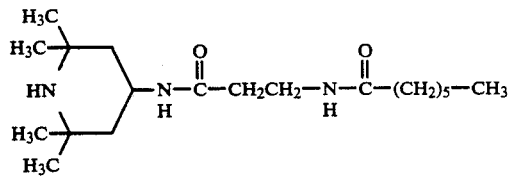

as a colorless solid of melting point 112° C.
Calculated: C 67.2 H 11.0 N 12.4 O 9.4%
Found: C 67.1 H 11.0 N 12.3 O 9.3%

EXAMPLE 25

34 g of the product of Example 2, 15 g of triethylamine and the acid chloride prepared from 24 g of lauric acid and 23.6 g of thionyl chloride were reacted and worked up, both steps being carried out as described in Example 24. This gave 45 g of the compound of the formula

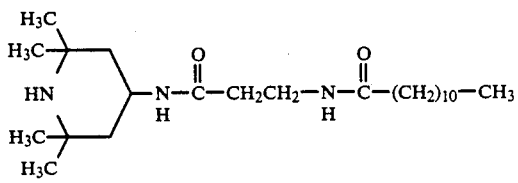

as a colorless solid of melting point 68° C.
Calculated: C 70.4 H 11.6 N 10.3 O 7.8%
Found: C 69.8 H 11.5 N 10.6 O 8.0%

EXAMPLE 26

34 g of the product of Example 2, 15 g of triethylamine and the acid chloride obtained from 42.7 g of stearic acid and 23.6 g of thionyl chloride were reacted and worked up, both steps being carried out as described in Example 24. This gave 51.3 g of the compound of the formula

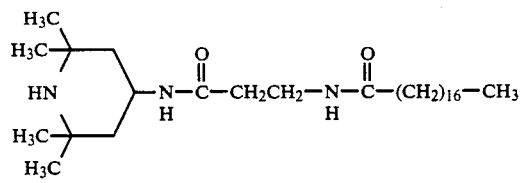

as a colorless solid of melting point 80° C.
Calculated: C 73.0 H 12.0 N 8.5 O 6.5%
Found: C 72.4 H 12.0 N 8.4 O 6.7%

EXAMPLE 27

44 g of the product of Example 2, 15 g of triethylamine and the acid chloride prepared from 20.4 g of 2-methylbenzoic acid and 23.6 g of thionyl chloride were reacted and worked up, both steps being carried out as described in Example 24. This gave 31.1 g of the compound of the formula

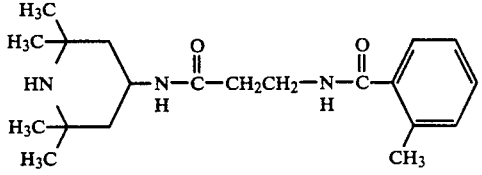

as a colorless solid of melting point 191° C.
Calculated: C 69.5 H 9.0 N 12.2 O 9.3%
Found: C 69.2 H 9.1 N 12.2 O 9.4%

EXAMPLE 28

26.3 g of 4-chlorobenzoyl chloride in 100 ml of dichloromethane were added dropwise at 0° C. to 34 g of the product of Example 2 and 15 g of triethylamine in 400 ml of dichloromethane. After 4 hours of stirring at room temperature, the resulting precipitate was filtered off with suction, washed with a little dichloromethane and dried. It was dissolved in water, the solution was rendered alkaline with sodium hydroxide solution, and the mixture was extracted with dichloromethane. The solvent was evaporated off, and the residue was recrystallized from acetonitrile. This gave 24.1 g of the compound of the formula

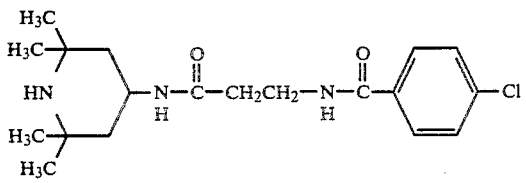

as a colorless solid of melting point 172° C.
 Calculated: C 62.4 H 7.7 Cl 9.7 N 11.5 O 8.7%
 Found: C 62.4 H 7.8 Cl 9.3 N 11.6 O 8.8%

EXAMPLE 29

12.5 g of the product of Example 2 and 7.4 g of phthalic anhydride were boiled in 150 ml of toluene for 7 hours under a water separator. The resulting precipitate was filtered off with suction while still hot, and dried. It amounted to 17.3 g of the compound of the formula

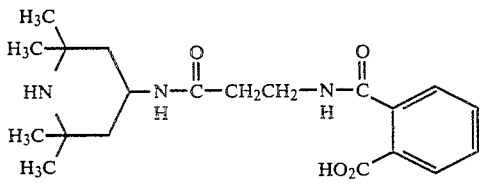

of melting point 212°–214° C. (dec.).
 Calculated: C 64.0 H 7.8 N 11.2 O 17.0%
 Found: C 63.9 H 8.1 N 11.2 O 16.7%

EXAMPLE 30

44 g of the product of Example 2, 15 of triethylamine and the acid chloride prepared from 20.4 g of 4-methylbenzoic acid and 23.6 g of thionyl chloride were reacted as in Example 24. After 4 hours the reaction mixture was filtered, and the filtrate was admixed with ice-water and sodium hydroxide solution and extracted with dichloromethane. After the dichloromethane had been distilled off, the residue was recrystallized from acetonitrile. This gave 13.8 g of the compound of the formula

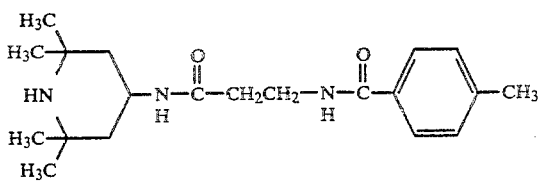

as a colorless solid of melting point 159°–160° C.
 Calculated: C 69.5 H 9.1 N 12.2 O 9.3%
 Found: C 69.4 H 9.3 N 12.3 O 8.8%

EXAMPLE 31

34 of the product of Example 2, 15 g of triethylamine and the acid chloride prepared from 21.6 g of octanoic acid and 23.6 g of thionyl chloride were reacted and worked up, both steps being carried out as described in Example 24. Recrystallization from acetonitrile gave 20.7 g of the compound of the formula

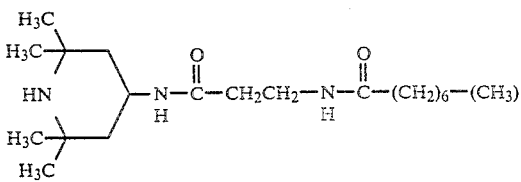

as a colorless solid of melting point 84° C.
 Calculated: C 67.9 H 11.1 N 11.9 O 9.1%
 Found: C 67.8 H 11.2 N 12.0 O 9.1%

EXAMPLE 32

45.4 g of the product of Example 2 and 42.9 g of ethyl undecanoate were boiled in 200 ml of ethanol for 2 hours. After 35 ml of 30% strength methanolic sodium methoxide solution had been added, heating at the boil was continued for a further 8 hours. After concentrating, the residue was stirred with 300 ml of actonitrile for 30 minutes. Insolubles were filtered off, the filtrate was concentrated, and the resulting residue was dispersed in 500 ml of water and 250 ml of dichloromethane. The phases were separated, and the dichloromethane phase was stripped of solvent, leaving as a residue 32.8 g of the compound of the formula

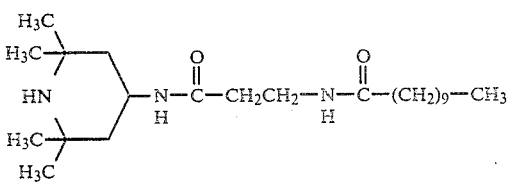

as a viscous mass which solidifies over a few days into a colorless solid of melting point 72°–75° C.
 Calculated: C 69.8 H 11.5 N 10.6 O 8.3%
 Found: C 69.4 H 11.5 N 10.9 O 8.3%

EXAMPLE 33

34 g of the product of Example 2, 15 of triethylamine and the acid chloride prepared from 22.8 g of 4-methoxybenzoic acid and 23.6 g of thionyl chloride were reacted and worked up, both steps being carried out as described in Example 24. Recrystallization from acetonitrile gave 30 g of the compound of the formula

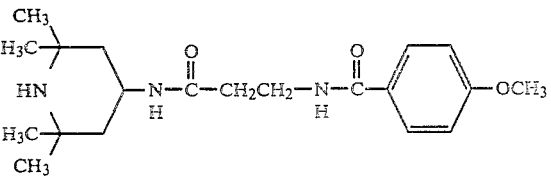

as a colorless solid of melting point 145°–147° C.
 Calculated: C 66.5 H 8.6 N 11.6 O 13.3%
 Found: C 66.3 H 8.6 N 11.4 O 13.2%

EXAMPLE 34

34 g of the product of Example 2, 15 g of triethylamine and the acid chloride prepared from 21 g of 2,4-dimethylfuran-3-carboxylic acid and 23.6 g of thionyl chloride were reacted and worked up, both steps being carried out as in described in Example 28. Recrystallization from acetonitrile gave 15.2 g of the compound of the formula

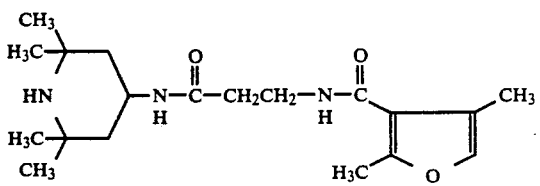

as a colorless solid of melting point 176° C.
Calculated: C 65.3 H 8.9 N 12.0 O 13.8%
Found: C 64.7 H 9.0 N 11.9 O 13.9%

EXAMPLE 35

46.3 g of the product of Example 2 were boiled in 250 ml of methyl formate in the presence of 3.6 g of 30% strength methanolic sodium methoxide solution for 9 hours. The resulting precipitate was filtered off with suction and dissolved in water, and the aqueous phase was extracted with n-butanol. The n-butanol phase was concentrated, and the residue was recrystallized from 6:1 acetonitrile/isopropanol, giving 19 g of the compound of the formula

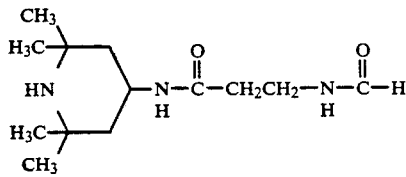

as a colorless solid of melting point 211° C.
Calculated: C 61.6 H 9.9 N 16.4 O 12.5%
Found: C 60.8 H 10.0 N 16.6 O 13.0%

EXAMPLE 36

34 g of the product of Example 2, 15 g of triethylamine and the acid chloride prepared from 17.1 g of cyclopentanecarboxylic acid and 23.6 g of thionyl chloride were reacted and worked up, both steps being carried out as described in Example 24. Recrystallization from acetonitrile gave 14 g of the compound of the formula

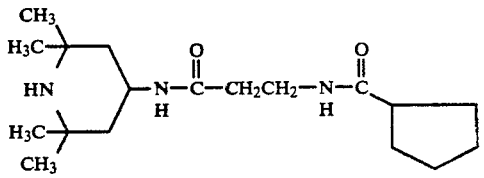

as a colorless solid of melting point 190° C.
Calculated: C 66.8 H 10.3 N 13.0 O 9.9%
Found: C 66.4 H 10.3 N 12.8 O 10.0%

EXAMPLE 37

34 g of the product of Example 2, 15 g of triethylamine and 23.8 g of 2,5-dimethylfuran-3-carbonyl chloride were reacted and worked up, both steps being carried out as described in Example 24. Recrystallization from acetonitrile gave 25.9 g of the compound of the

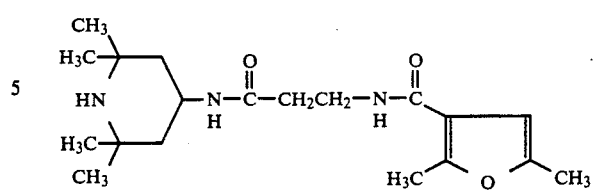

as a colorless solid of melting point 193°–194° C.
Calculated: C 65.3 H 8.9 N 12.0 O 13.8%
Found: C 65.3 H 8.6 N 11.9 O 13.8%

EXAMPLE 38

34 g of the product of Example 2, 15 g of triethylamine and the acid chloride prepared from 20.4 g of phenylacetic acid and 23.6 g of thionyl chloride were reacted and worked up, both steps being carried out as described in Example 24. Recrystallization from acetonitrile gave 12.7 g of the compound of the formula

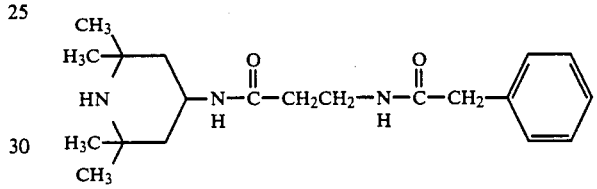

as a colorless solid of melting point 187°–188° C.
Calculated: C 69.5 H 9.0 N 12.2 O 9.3%
Found: C 67.3 H 8.9 N 11.7 O 12.0%

EXAMPLE 39

34 g of the product of Example 2, 15 g of triethylamine and the acid chloride prepared from 32.2 g of tridecanoic acid and 23.6 g of thionyl chloride were reacted and worked up, both steps being carried out as described in Example 24. Recrystallization from acetonitrile gave 38 g of the compound of the formula

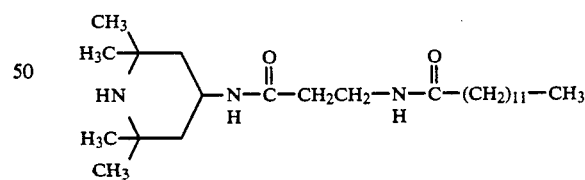

as a colorless solid of melting point 82° C.
Calculated: C 70.8 H 11.6 N 10.0 O 7.6%
Found: C 69.9 H 11.4 N 9.9 O 7.6%

EXAMPLE 40

34 g of the product of Example 2, 15 g of triethylamine and the acid chloride prepared from 22.8 g of phenoxyacetic acid and 23.6 g of thionyl chloride were reacted and worked up, both steps being carried out as described in Example 24. Recrystallization from acetonitrile gave 18.4 g of the compound of the formula

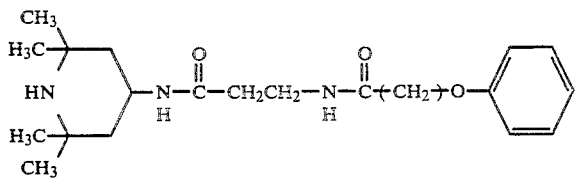

as a colorless solid of melting point 128°-130° C.
Calculated: C 66.5 H 8.6 N 11.6 O 13.3%
Found: C 65.6 H 8.4 N 11.4 O 13.8%

EXAMPLE 41

34.5 g of the product of Example 2, 15.2 g of triethylamine and 25.6 g of benzyl chloroformate were reacted and worked up, both steps being carried out as described in Example 20. The residue obtained on concentrating the organic phase was dissolved in hot ethyl acetate and treated with activated carbon. Filtration and concentration of the ethyl acetate phase gave 36 g of the compound of the formula

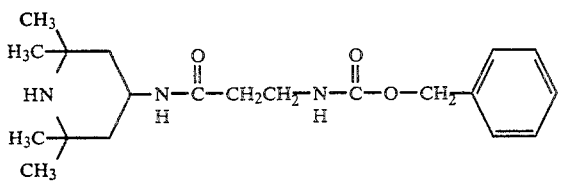

as a slightly tacky resin.
Calculated: C 66.4 H 8.6 N 11.6 O 13.3%
Found: C 66.3 H 8.7 N 11.5 O 14.2%

EXAMPLE 42

34 g of the product of Example 2, 15.1 g of triethylamine and 20.5 g of isobutyl chloroformate were reacted and worked up, both steps being carried out as described in Example 41. This gave 32 g of the compound of the formula

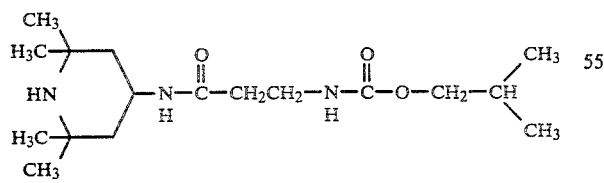

as a slightly tacky resin.
Calculated: C 62.3 H 10.1 N 12.8 O 14.6%
Found: C 62.4 H 10.3 N 12.6 O 15.1%

EXAMPLE 43

34.5 g of the product of Example 2, 15 g of triethylamine and 24.7 g of hexyl chloroformate were reacted and worked up, both steps being carried out as described in Example 41. This gave 41 g of the compound of the formula

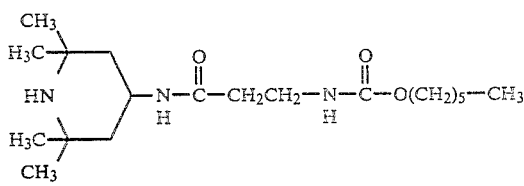

a slightly tacky resin.
Calculated: C 64.2 H 10.5 N 11.8 O 13.5%
Found: C 63.9 H 10.4 N 11.9 O 14.1%

EXAMPLE 44

34.5 g of the product of Example 2, 15.2 g of triethylamine and 24.4 g of cyclohexyl chloroformate were reacted and worked up, both steps being carried out as described in Example 20. Oil pump vacuum distillation gave 25.7 g of the compound of the formula

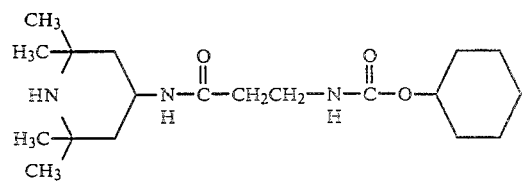

as a colorless oil of melting point 222°-224° C./0.3 mm Hg, which solidified into a colorless solid and on recrystallization from n-heptane had a melting point of 110° C.
Calculated: C 64.5 H 10.0 N 11.9 O 13.6%
Found: C 64.2 H 10.0 N 12.3 O 13.3%

EXAMPLE 45

34.2 g of the product of Example 2, 15 g of triethylamine and 18.2 g of 1,6-hexanediol bischloroformate were reacted and worked up, both steps being carried out as described in Example 41. This gave 26 g of the compound of the formula

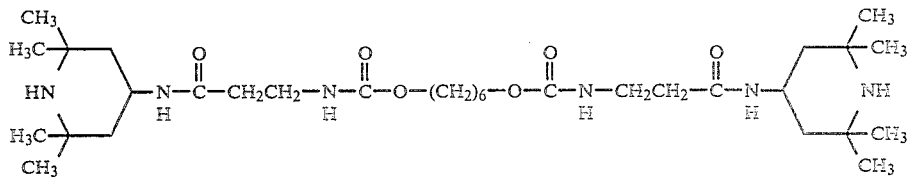

as a colorless solid of melting point 62° C.
Calculated: C 61.5 H 9.7 N 13.4 O 15.4%
Found: C 61.1 H 9.9 N 12.7 O 16.1%

EXAMPLE 46

37 g of phthalic anhydride, 56.8 g of the product of Example 2 and 16 g of Lewatit ® S 100 were boiled in 300 ml of xylene under a water separator until no further water came off. The mixture was filtered hot, and the filtrate was allowed to cool down to room temperature. The resulting precipitate amounted to 36.8 g of the compound of the formula

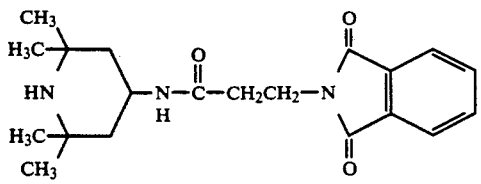
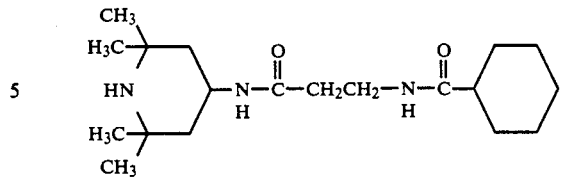

The colorless crystals had a melting point of 188° C.
Calculated: C 67.2 H 7.6 N 11.8 O 13.4%
Found: C 65.9 H 7.7 N 11.4 O 14.4%
The compound contains 0.5 mole of water of crystallization.

EXAMPLE 47

34 g of Example 2, 15 g of triethylamine and 29.5 g of 4-tert-butylbenzoyl chloride were reacted and worked up, both steps being carried out as described in Example 16. Recrystallization from toluene gave 31.4 g of the compound of the formula

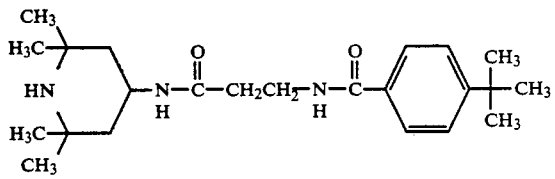

as a colorless solid of melting point 105°-107° C.

EXAMPLE 48

34 g of the product of Example 2, 15 g of triethylamine and the acid chloride prepared from 19.3 g of cyclohexanecarboxylic acid and 23.6 g of thionyl chloride were reacted and worked up, both steps being carried out as described in Example 16. Recrystallization from ethyl acetate gave 16.4 g of the compound of the formula as a colorless solid of melting point 175°-178° C.

EXAMPLE 49

34 g of the product of Example 2, 15 g of triethylamine and the acid chloride prepared from 24.9 g of 4-methoxyphenylacetic acid and 23.6 g of thionyl chloride were reacted and worked up, both steps being carried out as described in Example 24. Recrystallization from acetonitrile gave 24 g of the compound of the formula

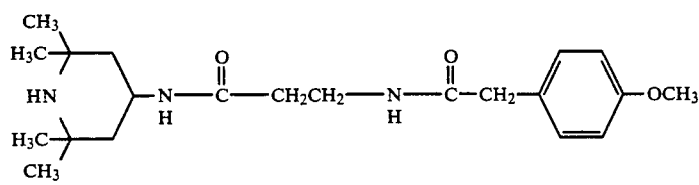

as a colorless solid of melting point 168°-169° C.

EXAMPLE 50

68 g of the product of Example 2, 30 g of triethylamine and the acid chloride prepared from 36.6 g of 1,11-undecanedicarboxylic acid and 47.2 g of thionyl chloride were reacted and worked up, both steps being carried out as described in Example 24. Recrystallization from acetonitrile gave 52.8 g of the compound of the formula

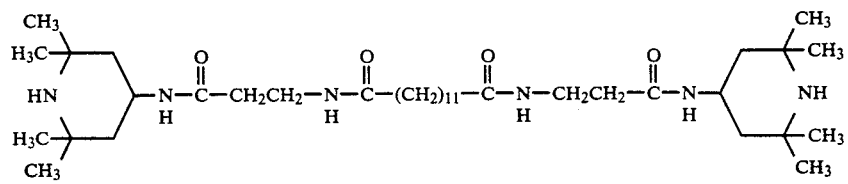

as a colorless solid of melting point 65°-67° C.

EXAMPLE 51

16.9 g of nonanedioyl chloride were added to a solution of 34 g of the product of Example 2 and 15 g of triethylamine in 400 ml of dichloromethane. After 16 hours of stirring, ice-water was added, the mixture was rendered alkaline with sodium hydroxide solution, the phases were separated, and the organic phase was concentrated. The remaining residue was recrystallized from acetonitrile, to give 5.6 g of the compound of the formula

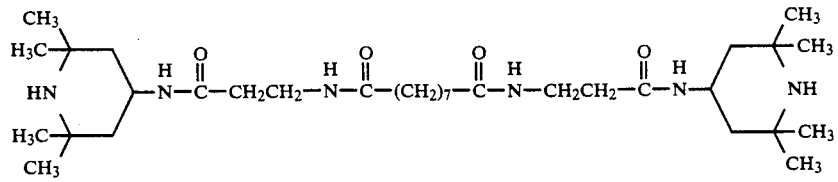

as a colorless dihydrate of melting point 90°-94° C.
Calculated: C 61.6 H 10.3 N 13.1 O 14.9
Found: C 61.6 H 10.4 N 12.6 O 14.8

EXAMPLE 52

A solution of 15.7 g of cyclopropanecarbonyl chloride in 100 ml of dichloromethane was added dropwise to a solution of 34 g of the product of Example 2 and 15 g of triethylamine in 200 ml of dichloromethane. After 16 hours of stirring, ice-water was added, the mixture was rendered alkaline with sodium hydroxide solution, the organic phase was separated off, and the aqueous phase was extracted with n-butanol. The organic phases were concentrated, giving 36 g of a crude product of melting point 175°-178° C. Recrystallization from ethyl acetate gave 12.8 g of the compound of the formula

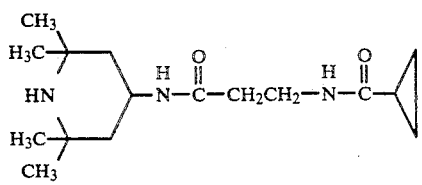

of melting point 187°-188° C.
Calculated: C 65.1 H 9.9 N 14.2 O 10.8
Found: C 64.8 H 10.0 N 14.1 O 11.0

EXAMPLE 53

56.8 g of the product of Example 1 and 49.5 g of 1,8-naphthalenedicarboxylic anhydride were boiled in 300 ml of xylene under a water separator for 36 hours. The reaction mixture was filtered hot, and the precipitate resulting in the filtrate was filtered off with suction, giving 70 g of a crude product of melting point 178°-180° C. Recrystallization from acetonitrile gave 32.6 g of the compound of the formula

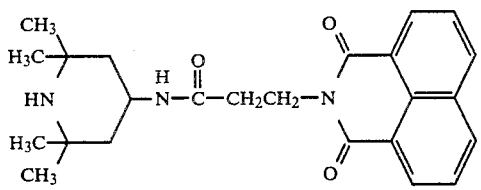

as a colorless hemihydrate of melting point 182° C.
Calculated: C 69.2 H 7.3 N 10.1 O 13.4
Found: C 68.9 H 7.3 N 10.4 O 13.2

USE EXAMPLE

Stabilization of polyamide (a) 0.2 part of the product of Example 16 was incorporated into 100 parts of commercial polyamide (Ultramid B3S from BASF) by single extrusion at 250° C., and the resulting granules were injection-molded at 250° C. into 2 mm thick test specimens.

(b) The test specimens produced by (a) were tested in a Xenotest ® 1200 accelerated weathering tester in respect of light and weathering fastness. Aging was determined by measuring the time to the onset of crack formation at the surface of the test specimen.

The test specimens produced by (a) still showed no cracks in the surface after 2000 hours of weathering, while analogous test specimens without stabilizer showed cracks after as little as 750 hours of weathering.

We claim:
1. A compound of the formula (I)

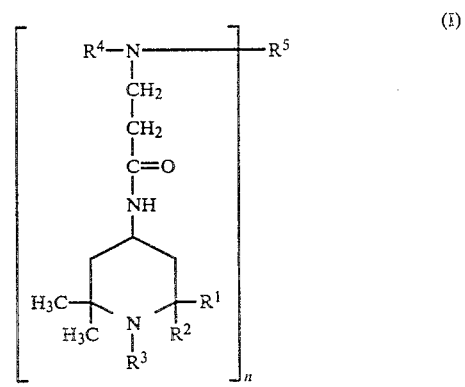

where
$R^1$ and $R^2$ are singly methyl or together tetramethylene or pentamethylene,
$R^3$ is hydrogen, $C_1$-$C_8$-alkyl, $C_1$-$C_8$-alkoxycarbonyl $C_1$-$C_8$-alkanoyl, benzyl, hydroxyethyl, cyanomethyl or aminoethyl,
n is 1, 2 or 3, and—
when n is 1—
$R^4$ is hydrogen and
$R^5$ is (a) 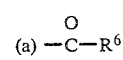

where
$R^5$ is hydrogen, $C_1$-$C_{19}$-alkyl, $C_7$-$C_{10}$-phenylalkyl where the phenyl nucleus is unsubstituted or monosubstituted, disubstituted or trisubstituted by $C_1$-$C_8$-alkyl, chlorine, bromine, fluorine, hydroxyl, $C_1$-$C_4$-alkoxy, phenyl, phenoxy or carboxyl and the substituents can be identical or different, phenoxy-$C_1$-$C_4$-alkyl, unsubstituted or $C_1$-$C_8$-alkyl-monosubstituted, -disubstituted or -trisubstituted $C_3$-$C_{10}$-cycloalkyl, unsubstituted or $C_1$-$C_8$-alkyl-, chlorine-, bromine-, fluorine-, hydroxyl-, $C_1$-$C_4$-alkoxy-, phenyl-, phenoxy- or carboxyl-monosubstituted, -disubstituted or -trisubstituted phenyl or naphthyl, furan, thiophene or pyridine, unsubstituted or monosubstituted, disubstituted, trisubstituted or tetrasubstituted by $C_1$-$C_4$-alkyl, or $C_1$-$C_{18}$-alkoxy where the alkyl chain may be interrupted by —O—, or phenoxy, naphthoxy, unsubstituted or $C_1$-$C_4$-alkylmonosubstituted or -disubstituted $C_5$- or $C_6$-cycloalkoxy or phenylalkoxy of from 7 to 12 carbon atoms in total, (b) —CO—NH—$R^7$ where $R^7$ is hydrogen, $C_1$-$C_{18}$-alkyl, $C_5$- or $C_6$-cycloalkyl, phenyl which may be monosubstituted, disubstituted or trisubstituted by $C_1$-$C_8$-alkyl, chlorine, bromine, fluorine or $C_1$-$C_4$-alkoxy, or phenyl-$C_1$-$C_4$-alkyl, or (c) —$SO_2$—$R^8$ where $R^8$ is $C_1$-$C_{18}$-alkyl or unsubstituted or $C_1$-$C_4$-alkyl- or chlorine-substituted phenyl, or $-N\begin{smallmatrix}R^4\\R^5\end{smallmatrix}$ is 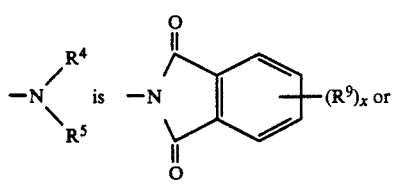 $(R^9)_x$ or

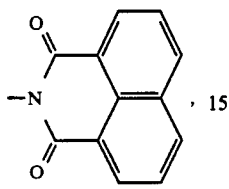, where $R^9$ is $C_1$-$C_8$-alkyl, chlorine, bromine or fluorine and x is 0, 1, 2, 3 or 4, or - when n is 2—

$R^4$ is hydrogen and
$R^5$ is

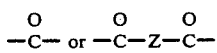

where

Z is a chemical bond, $C_1$-$C_{12}$-alkylene, $C_4$-$C_8$-oxaalkylene, phenylene, cyclohexylene, biphenylene, biphenylene oxide, dioxyphenylene, diaminophenylene, diaminocyclohexylene, $$-N\overset{H}{-}(CH_2)_{\overline{u}}NH-$$

where u is from 2 to 6, —O—X—O—, where X is $C_2$-$C_8$-alkylene or $C_4$-$C_8$-oxaalkylene, furan, thiophene or pyridine unsubstituted or monosubstituted, disubstituted, trisubstituted or tetrasubstituted by $C_1$-$C_4$-alkyl, or $C_1$-$C_{18}$-alkoxy where the alkyl chain may be interrupted by —O—, or phenoxy, naphthoxy, unsubstituted or $C_1$-$C_4$-alkylmonosubstituted or -disubstituted $C_5$- or $C_6$-cycloalkoxy or phenylalkoxy of from 7 to 12 carbon atoms in total, or

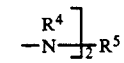

is a pyromellitimide group, or—when n is 3—
$R^4$ is hydrogen and
$R^5$ is $$-\begin{bmatrix}O\\C\end{bmatrix}_3-R^{10},$$

where
$R^{10}$ is trivalent $C_1$-$C_8$-alkyl or trivalent aryl, or an acid addition salt or hydrate thereof.

2. A compound as claimed in claim 1, wherein $R^1$ and $R^2$ are each methyl.

3. A compound as claimed in claim 1, wherein $R^3$ is hydrogen.

4. A compound as claimed in claim 2, wherein $R^3$ is hydrogen.

* * * * *